(12) United States Patent
Serban et al.

(10) Patent No.: US 7,913,541 B2
(45) Date of Patent: Mar. 29, 2011

(54) MATRIX NANOCOMPOSITE CONTAINING AMINOCARBON NANOTUBES FOR CARBON DIOXIDE SENSOR DETECTION

(75) Inventors: Bogdan Catalin Serban, Bucharest (RO); Cornel P. Cobianu, Bucharest (RO); Mircea Bercu, Bucharest (RO); Nicolae Varachiu, Bucharest (RO); Mihai N. Mihaila, Bucharest (RO); Cazimir G. Bostan, Bucharest (RO); Stefan Ioan Voicu, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 631 days.

(21) Appl. No.: 11/799,372

(22) Filed: Apr. 30, 2007

(65) Prior Publication Data

US 2008/0264147 A1   Oct. 30, 2008

(51) Int. Cl.
*G01N 29/02*   (2006.01)
(52) U.S. Cl. ............ 73/24.06; 73/24.01; 73/31.01; 73/31.05; 977/745; 977/953; 977/957
(58) Field of Classification Search ............ None
See application file for complete search history.

(56) References Cited

U.S. PATENT DOCUMENTS

| 6,420,293 | B1 | 7/2002 | Chang et al. | |
| 2003/0089893 | A1* | 5/2003 | Niu et al. | 252/500 |
| 2005/0129573 | A1 | 6/2005 | Gabriel et al. | |
| 2006/0252853 | A1 | 11/2006 | Ajayan et al. | |
| 2008/0093226 | A1* | 4/2008 | Briman et al. | 205/775 |
| 2008/0216558 | A1* | 9/2008 | Koyilothu et al. | 73/24.06 |
| 2009/0260423 | A1* | 10/2009 | Munoz et al. | 73/61.71 |

FOREIGN PATENT DOCUMENTS

| WO | WO 02/18296 A1 | 3/2002 |
| WO | WO 2005/026694 A2 | 3/2005 |
| WO | WO 2005/026694 A3 | 3/2005 |

OTHER PUBLICATIONS

Advances in SAW-Based Gas Sensors, C. Caliendo, P. Verardi, E. Verona, A D'Amico, DiNatale, G. Saggio, M. Serafini, R. Paolesse, S.E. Huq; Smart Mater. Struct. 6 (1997) 689-699.

Nanocomposites Based on Conducting Polymers and Carbon Nanotubes from Fancy Materials to Functional Applications; M. Baibarac, P. Gomez-Romero; Journal of Nanoscience and Nanotechnology vol. 6, 1-14, 2006.

Polymer Coatings of Carbon Nanotube Sensors; A. Star, TR Han, V. Joshi, G. Gruner; Polymer Preprints 2003, 44(2), 2001.

(Continued)

*Primary Examiner* — Daniel S Larkin
(74) *Attorney, Agent, or Firm* — Kermit D. Lopez; Luis M. Ortiz; Kris T. Fredrick (57) ABSTRACT

The design and synthesis of a matrix nanocomposite containing amino carbon nanotubes used as a functionalized sensing layer for carbon dioxide detection by means acoustic wave sensing devices, e.g., SAW/BAW devices. These sensing materials contain a type of amino carbon nanotubes (single walled or multi-walled) and a polymer (or other compounds) which are sensitive to carbon dioxide in the acoustic wave sensing device based gas sensors. The sensitivity of the matrix consisting of the amino carbon nanotubes and a polymer (or other compounds) is ensured by the presence of amino groups which can react at room temperature with $CO_2$ in a reversible process to form carbamates.

10 Claims, 9 Drawing Sheets

OTHER PUBLICATIONS

Chemistry of Single-Walled Carbon Nanotubes; S. Niyogi, M.A. Hamon, H. Hu, B. Zhao, P. Bhowmik, R. Sen, M.E. Itkis, R.C. Haddon; vol. 35, No. 12, 2002; Accounts of Chemical Research.

Sidewall Amino-Functionalization of Single-Walled Carbon Nanotubes Through Fluorination and Subsequent Reactions with Terminal Diamines; J.L. Stevens, A.Y. Huang, H. Peng, I.W. Chiang, V.N. Khabashesku, J. L. Margrave; Nano Letters 2003 vol. 3 No. 3, 331-336.

Covalent Amino-Functionalisation of Single-Wall Carbon Nanotubes; A. Gromov, S. Dittmer, J. Svensson, O.A. Nerushev, S. A. Perez-Garcia, L Licea-Jimenez, R. Rychwalski, E. E.B. Campbell; J. Mater. Chem., 2005, 15, 3334-3339.

Amino-Functionalized Carbon Nanotubes for Binding to Polymers and Biological Systems; T. Ramanathan, F.T. Fisher, R.S. Ruoff, L.C. Brinson; Chem. Mater. 2005, 17, 1290-1295.

Chemical Sensor Technologies, Tutorial 2006; A Lloyd Spetz; S-SENCE/IFM Linkoping University, 581 83 Linkoping, Sweden Chemically Functionalized Carbon Nanotubes; K. Balasubramanian, M. Burghad; Small 2005, 1, No. 2, 180-192.

Carbon Nanotubes as Polymer Antioxidants; P.C.P. Watts, P.K. Fearon, W.K. Hsu, N.C. Billingham, H.W> Kroto and D.R.M. Walton; J. Mater. Chem, 2003, 13, 491-495.

Flourination of Single-Wall Carbon Nanotubes and Subsequent Derivatization Reactions; V.N. Khabashesku, W. E. Billups, J.L. Margrave; vol. 35, No. 12, 2002, Accounts of Chemical Research.

Nanoelectronic Carbon Dioxide Sensors; A. Star, T.R. Han, V. Joshi, JC P. Gabriel, G. Gruner; Adv. Mater. 2004, 16, No. 22, Nov. 18, 2049-2052.

Preliminary Results with a Silicon-Based Surface Acoustic Wave Chemical Sensor for No2; M.S. Nieuwenhuizen, A.J. Nederlof, M.J. Vellekoop, A. Venema; Sensors and Actuators, 19 (1989) 385-392.

Harmonic Frequency Analysis of SAW Resonator Chemical Sensors; Application to the Detection of Carbon Dioxide And Humidity; K. Korsah, C.L. Ma, B. Dress; Sensors and Actuators B 50 (1998) 110-116.

* cited by examiner

MATRIX NANOCOMPOSITE CONTAINING AMINOCARBON NANOTUBES FOR CARBON DIOXIDE SENSOR DETECTION

TECHNICAL FIELD

Embodiments are generally related to matrix nanocomposites comprising amino carbon nanotubes for carbon dioxide sensors. Embodiments are also related to a method of designing and synthesizing of matrix nanocomposites for acoustic wave sensing devices (e.g., SAW/BAW sensors) used in carbon dioxide detection.

BACKGROUND OF THE INVENTION

Carbon nanotubes (CNT) are cylindrical carbon molecules with a diameter of a few nanometers. Due to their tubular structure and unique dimensions, carbon nanotubes exhibit remarkable electrical, thermal, chemical and mechanical properties. In the last decade, the CNTs have become a very important material for different domains like electronics, optoelectronics, automation and control fields, for current or potential applications such as: electrochemical capacitors, sensors (gas sensors and biosensors), field-emission displays, solar cells, transistors, Schottky diodes, photovoltaic cells and photodiodes, composite fiber in polymers and ceramics. The CNT can be classified into two types: single-walled carbon nanotubes and multi-walled carbon nanotubes.

Manufacturing of CNT based devices is still in the early stages due to present technological challenges like: insolubility of parent carbon nanotubes in most common organic solvents and low processing capabilities. Recently, in order to improve CNT solubility in water and organic solvents, and also the chemical compatibility with polymers and ceramics, CNT functionalization has been proposed as a possible technological thrust. Noncovalent functionalization implies $\pi$-$\pi$ stacking interactions between the surface of carbon nanotubes and aromatic molecules such as benzene or styrene. As a major advantage, non-covalent functionalization preserves mechanical and electrical properties. However, the forces between carbon nanotubes and wrapping molecules may be weak. In the case of covalent functionalization, the attachment of molecule at the surface of carbon nanotubes is strong (covalent bond), but this type of functionalization introduces defects in the structure of CNTs and can affect the electrical and mechanical properties of CNTs. For example, if the carbon nanotubes are sonicated in the presence of detergent molecules they disperse to create a suspension with limited stability. Several procedures have been developed in order to modify the structure of carbon nanotubes and to link at its surface some reactive groups such as: carboxylic groups, phenolic groups, amino groups, etc.

The derivatization through covalent functionalization of carbon nanotubes (single walled and multi-walled carbon nanotubes) with amino groups (or with amino and sulfonic groups) opens perspectives for the synthesis of novel carbon nanotubes which can be the precursors for the design of new molecular architectures. Amino carbon nanotubes can be synthesized by sonicating carbon nanotubes in $HNO_3$ in order to create carboxyl groups at the surface, treating the resulting carboxycarbon nanotubes with thionyl chloride and synthesizing the corresponding amino carbon nanotubes through the intermediate of ammonia. Finally, Hoffman degradation in presence of natrium hypo bromide yields desirable amino carbon nanotubes.

An alternative procedure of CNT functionalization consists in the reaction between the acid chloride and carbon nanotubes with sodium azide followed by Curtius rearrangement. Also, synthesis of single-walled carbon nanotubes with amino methyl group ($CH_2NH_2$) has been reported. Recent publications relate synthesis of amino carbon nanotubes (single-walled and multi-walled) by means of nucleophilic substitution from fluorinated carbon nanotubes (synthesized from carbon nanotubes and fluorine at temperature>1500C) and alkyl amine. Additionally, it is possible to connect two fluorinated carbon nanotubes in a nucleophilic substitution reaction with a, w aliphatic diamine such as hexamethyleneamine, cadaverine or putresceine.

Many efforts have been made in order to improve the mechanical, electrical and chemical properties of polymers. Thus, one direction was to incorporate (carbon nanotubes (single-walled or multi-walled)) in the bulk of polymers. In the preparation of matrix composite CNTs/polymer, CNTs (modified or unmodified) were combined with conducting organic polymers (such as polyanilines (PANI), poly (3-,4-ethylenedioxy thiophenes), polypyrroles, polythiophenes, poly (p-phenylene vinylene), or with insulators polymers such as polycarbonates, polyethylene terephthalates, polystyrenes, polyphenylenesulphides, polysulfones, nylons, or copolymers such as poly (butylene adipate)-co-(amino caproate).

Incorporation of carbon nanotubes in polymers represents a remarkable way to improve electrical properties (in the case of conducting polymers through the $\pi$-$\pi$ stacking interactions), or mechanical properties. Moreover if the carbon nanotubes are added in the host matrix of polymer it is possible to tailor the chemical properties or physical properties for future applications (sensitivity for different type of gas molecules, compression modulus, and capacity of energy storage).

Like fullerenes, carbon nanotubes have high electron affinity and thus can act as an agents trapping radicals. Due to this property CNTs have a similar behavior with that of an anti-oxidant. Boron-doped carbon nanotubes can be used with good results for such a role too. Thus incorporation of CNTs in polymeric materials decreases the level of free radicals and increases the lifetime of polymers.

Carbon dioxide is a molecule with low reactivity, which and this is why it is difficult to sense. The sensing of carbon dioxide has a paramount importance in a broad variety of applications in hospitals (for capnography), in the management of building air, in chemical industry and in agriculture. For these applications the current technology-infrared spectroscopy is limited by its power consumption and size. Detection of carbon dioxide with SAW/BAW sensors represents an alternative which offers, for example, great sensitivity. In order to satisfy these demands active efforts have been made in the recent years to develop new $CO_2$-sensitive coatings for SAW/BAW sensors.

Phthalocyanine (PC) can be useful for carbon dioxide detection. Versamid 900, Polyethyleneimine (PEI), and BMBT (N,N bis-(p-methoxybenzylidene)-$\alpha$-$\alpha$'-bi-p-toluidine represent three polymers which were tested for the detection of carbon dioxide with SAW sensors. Among these polymers, the present inventors have found that PEI seems to show the best sensitivity (a frequency shift of about 1 kHz was measured for a concentration of 240 ppm of carbon dioxide in nitrogen). Primary, secondary and tertiary amino groups that exist in PEI are responsible enhanced sensing because amino groups react at room temperature with carbon dioxide and yield carbamates. The response time is of a few seconds and the chemical reaction is reversible.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved matrix nanocomposite containing amino carbon nanotubes for carbon dioxide SAW/BAW sensors.

It is another aspect of the present invention to provide a method of designing and synthesizing of matrix nanocomposites for SAW/BAW sensors used in carbon dioxide detection.

The aforementioned aspects and other objectives and advantages can now be achieved as described herein. The present invention relates to the design and synthesis of a matrix nanocomposite containing amino carbon nanotubes to be used as a functionalized sensing layer for carbon dioxide detection by means of acoustic wave sensing devices (e.g., SAW/BAW sensors). These sensing materials contain at least one type of amino carbon nanotubes (single walled or multi-walled) and a polymer (or other compounds) which are sensitive to carbon dioxide in the acoustic sensing device-based gas sensors. The sensitivity of the matrix comprising of the amino carbon nanotubes and a polymer (or other compounds) is ensured by the presence of amino groups which can react at room temperature with $CO_2$ in a reversible process to form carbamates.

Three approaches to construct matrix nanocomposite comprising amino carbon nanotubes for carbon dioxide acoustic wave detection are disclosed. The three approaches are design of matrix nanocomposite based on amino derivatives and amino CNTs without electric interaction between the two components, design of matrix nanocomposite based on amino derivatives and amino CNTs with electric interaction between the two components and design of matrix nanocomposite with incorporation of amino carbon nanotubes in polymer. The advantage of matrix nanocomposite is that amino groups in carbon nanotubes that enhance sensing and because of the size of CNTs many amino groups are present at the surface of layer of the sensor. Furthermore CNTs improve mechanical properties and can increase the lifetime of polymers due to the antioxidant character.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

The present invention is concerned with improving the design of a matrix nanocomposite comprising amino carbon nanotubes to be used as a functionalized sensing layer for carbon dioxide detection by means of SAW/BAW sending devices. These sensing materials comprise at least one type of amino carbon nanotubes (single-walled or multi-walled) combined with a polymer (or other compounds), wherein the amino carbon nanotube are sensitive to carbon dioxide when used as the sensing medium in SAW/BAW based gas sensors, whose basic physical structure is well known in the art. The sensitivity of a matrix comprising of the amino carbon nanotubes and a polymer (or other compounds) is ensured by the presence of amino groups which can react at room temperature with $CO_2$ in a reversible process to form carbamates.

Figure 1:
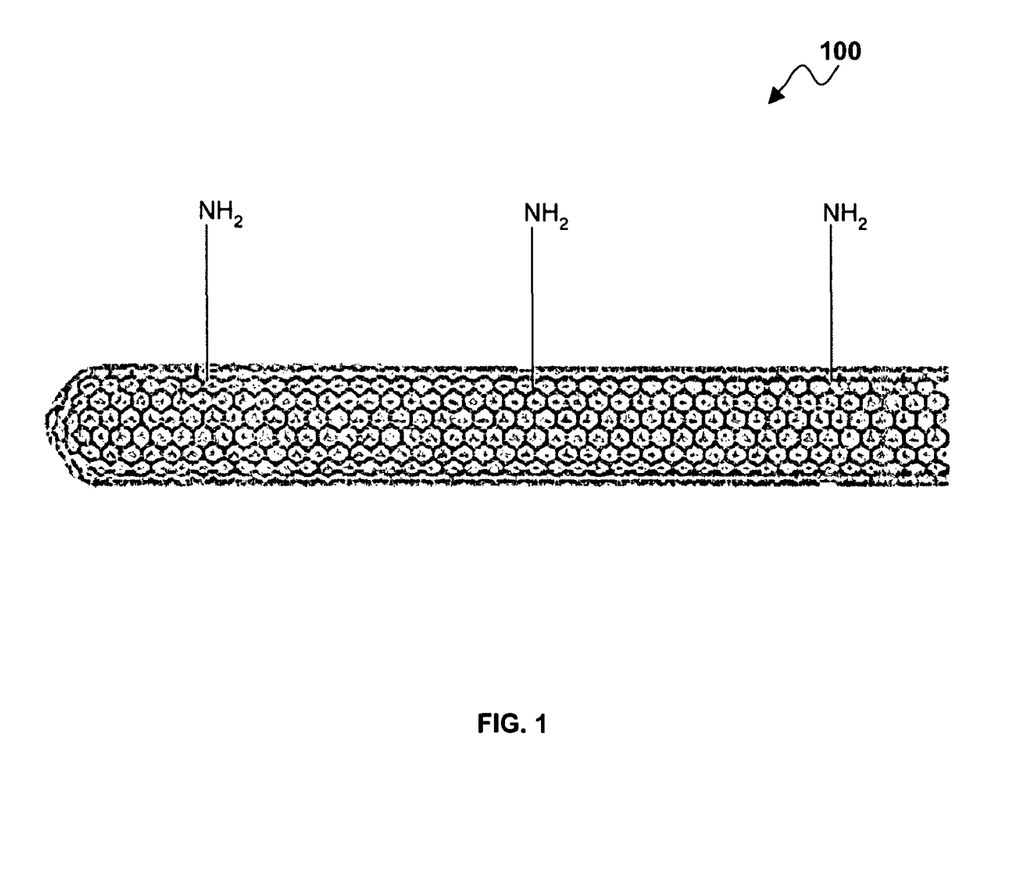
FIG. 1 illustrates structure of amino carbon nanotubes which can be implemented in accordance with a preferred embodiment.
Figure 2:
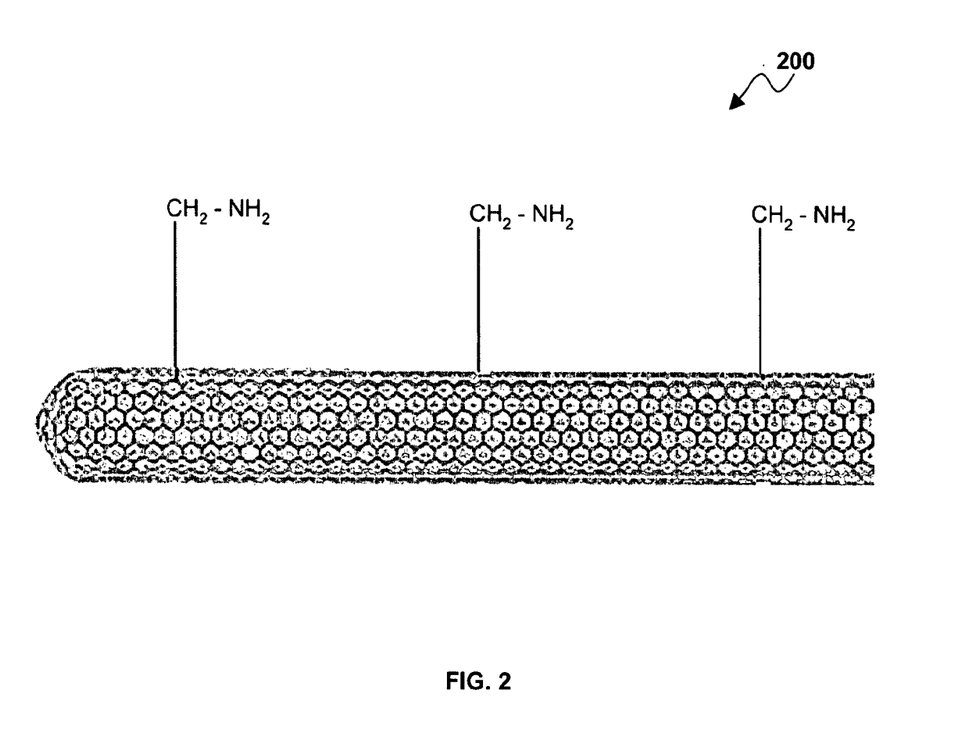
FIG. 2 illustrates structure of aminomethylcarbon nanotubes, which can be implemented in accordance with a preferred embodiment.
Figure 3:
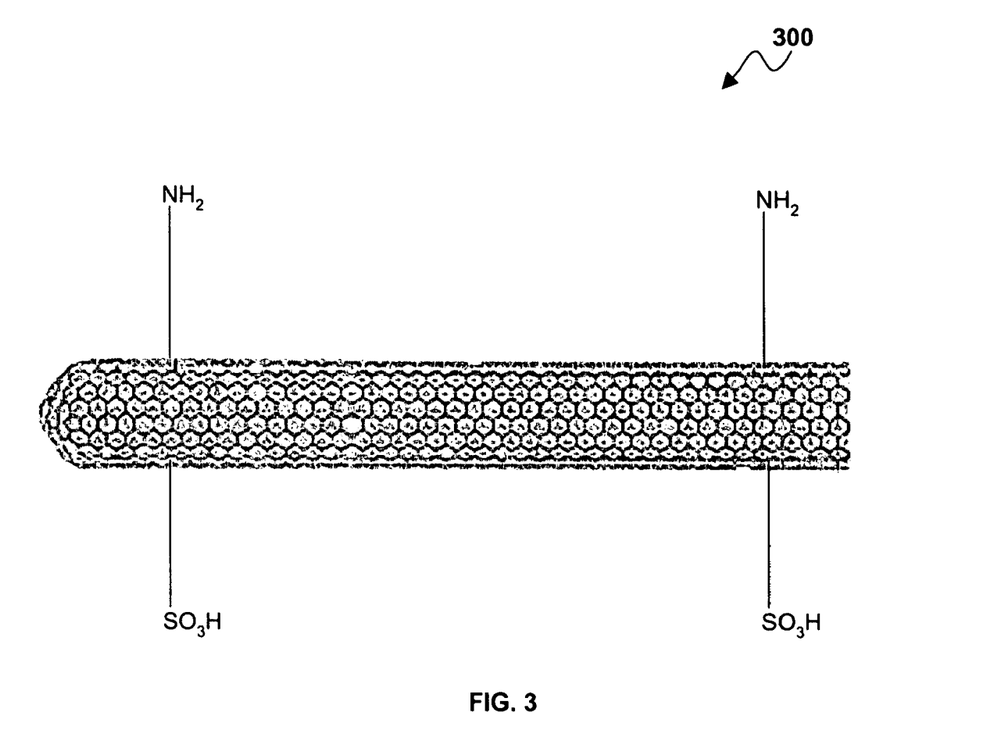
FIG. 3 illustrates structure of aminosulfonic carbon nanotubes, which can be implemented in accordance with a preferred embodiment.

The invention can use four types of CNT's that have amino groups directly or indirectly attached to the CNTs surface. The four types of CNTs are: CNTs with amino groups (amino carbon nanotubes), CNTs with amino methyl group (aminomethylcarbon nanotubes), CNTs with amino and sulfonic groups (aminosulfonic nanotubes) and CNTs linked through a spacer. Referring to FIGS. 1-3, illustrated are structures 100, 200 and 300, respectively, of amino carbon nanotubes, amiomethylcarbon nanotubes, and aminosulfonic nanotubes, which can be implemented in accordance with a preferred embodiment. Polyethylene imines (PEI), Versamid 900, BMBT (N,N bis-(p-methoxybenzylidene)-α-α'-bi-p-toluidine), polyallylamines, polyvinyl amines, diethanolamines, tryethanolamines and phthalocyanines (PC) can be used as polymers.

Figure 4:
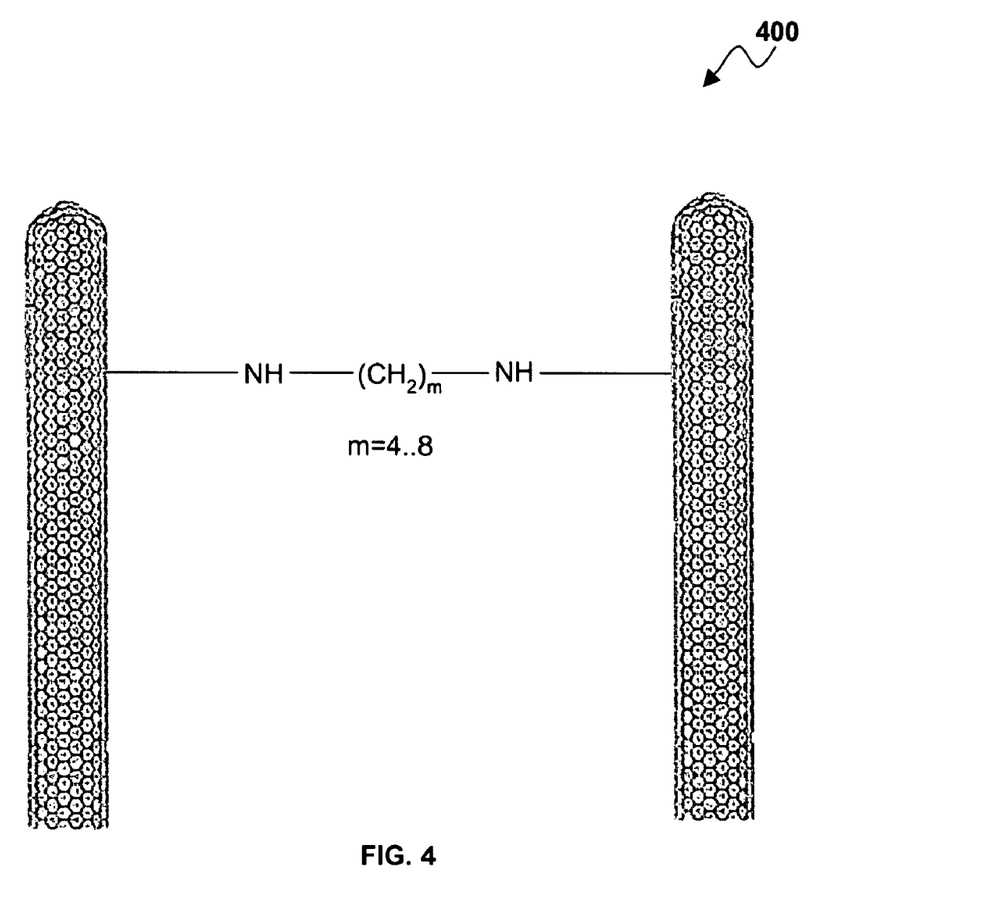
FIG. 4 illustrates structure of amino carbon nanotubes linked through a spacer, which can be implemented in accordance with a preferred embodiment.

FIG. 4 illustrates a structure 400 of carbon nanotubes linked through a spacer, which can be implemented in accordance with a preferred embodiment. A rearrangement of two nanotubes connected with α ω, aliphatic diamines such as hexamethyleneamine, cadaverine and putresceine is shown in FIG. 4. The covalently functionalized nanotubes can be single-walled or double-walled.

Three chemical routes can be used to construct the matrix nanocomposite comprising amino carbon nanotubes for carbon dioxide detection by means of SAW/BAW devices. The three chemical routes are designed of a matrix nanocomposite based on amino derivatives and amino CNTs without electric interaction between the two components, design of matrix nanocomposite based on amino derivatives and amino CNTs with electric interaction between the two components and design of matrix nanocomposite with incorporation of amino nanotubes into/onto a polymer.

In the design of a matrix nanocomposite based on amino derivatives and amino CNTs without electric interaction between the two components, the inventors constructed a nanocomposite by dispersing and sonicating a solution of amino CNTs in an appropriate solvent and mixed with a solution of polymer. Amino carbon nanotubes were present in a composite in 5-15% (w/w).

EXAMPLE 1

A solution of polyethyleneimine in dimethiyformamide (10 grams in 250 mL solvent was prepared) was taken. Another solution of amino carbon nanotubes (1 gram in 150 ml solvent) was placed in an ultrasonical bath and was sonicated for eight hours, in order to disperse the aggregated CNTs. After that, both solutions were mixed and spinned onto the surface of piezoelectric quartz to from a matrix nanocomposite.

The resulting nanocomposite had advantages in comparison with usual solution (PEI). After mixing the above solutions the carbon nanotubes have amino group which in addition can help to sensing. Due to the size of CNT many amino groups are present at the surface of layer. CNT is a well-known hydrophobic material and thus can reduce the cross-sensitivity due to humidity. PEI show good response for carbon dioxide molecules. Furthermore, CNT's can improve mechanical properties and can increase the life time of polymer due to the antioxidant character.

In design of a matrix nanocomposite based on amino derivatives and amino CNTs with electric interaction between the two components, the semiconductor polymers that are sensitive for carbon dioxide detection are doped polyanilines with protonic acid HA in an acid-base equilibrium. The dopant HA possesses large organic counter-ions such as sulfonated crown ethers, cyclodextrins, fullerenes etc. Some of them are 3'-sulfobenzo-12-crown-4(SB12C4), 3'-sulfobenzo-15-crown-5 (SB15C5), 3'-sulfobenzo-18-crown-6(SB18C6), di(3'-sulfo)dibenzo-18-crown-6 (DSDB18C6), di(3'-sulfo)-dibenzo-21-crown-67 (DSDB21C7), di(3'-sulfo)-dibenzo-24-crown-8 (DSDB24C8)), carboxylic acid of calix[n]arenes, carboxylic acid of fullerenes, sulfonatocyclodextrines (alfa, beta, gamma), dibenzo-21-crown-67(DSDB21C7), di (3'-sulfo)-dibenzo-24-crown-8 (DSDB24C8). sulfonato amino amino carbon nanotubes.

One of the two approaches to design matrix nanocomposite based on amino derivatives and amino CNTs with electric interaction between the two components comprises of synthesizing a nanocomposite based on doped polyanilines with protonic acid HA and combining with amino carbon nanotubes. The carbon nanotubes can be used in the nanocomposites one by one. Another way is to use a polyaniline doped with sulfonato amino CNTs and mixed after that with the other type of amino carbon nanotube.

EXAMPLE 2

Figure 5:
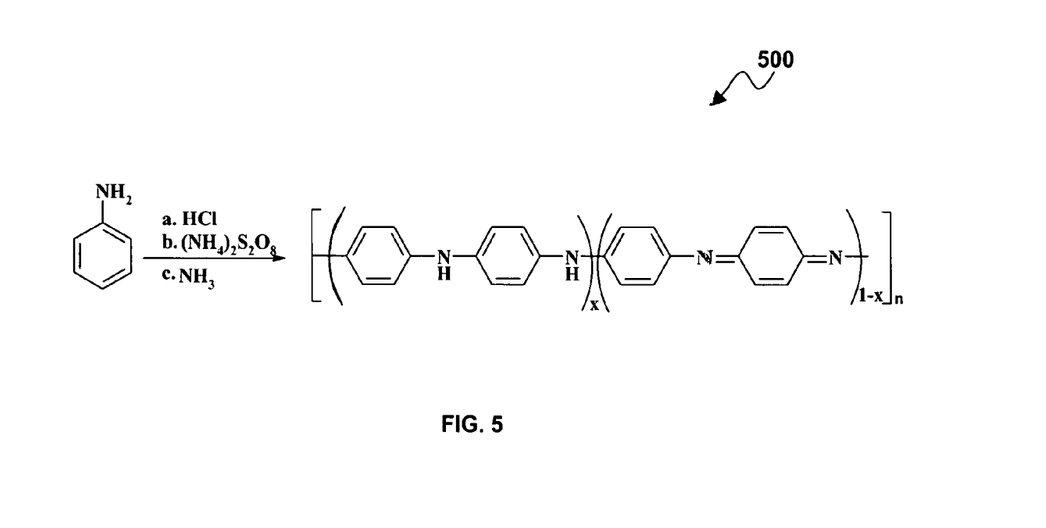
FIG. 5 illustrates a scheme for the synthesis of emeraldine, which can be implemented in accordance with a preferred embodiment.

Referring to FIG. 5, illustrated is a scheme for the synthesis of emeraldine/polyaniline, which can be implemented in accordance with a preferred embodiment. Polyaniline was prepared by chemical oxidation of aniline with ammonium peroxodisulphate. Aniline (23.3 g, 0.25 ml) was dissolved in 150 ml water, and then 20 ml of 37.5% hydrochloric acid was added to it. The mixture was stirred in an ice bath for one hour. Polymerization was started by addition of ammonium peroxodisulphate (57 g, 0.25 mol). After addition of ammonium peroxodisulphate, the solution was covered and placed in a refrigerator, at 0 degree Celsius, for six hours. After this, the mixture was diluted with water, and precipitate was filtered, washed with an excess of 0.5 M ammonium hydroxide, and then washed with deionizated water. The resulting polyaniline, a dark powder, was dried under 60 degree Celsius, for six hours, in order to remove the solvent and water.

Figure 6:
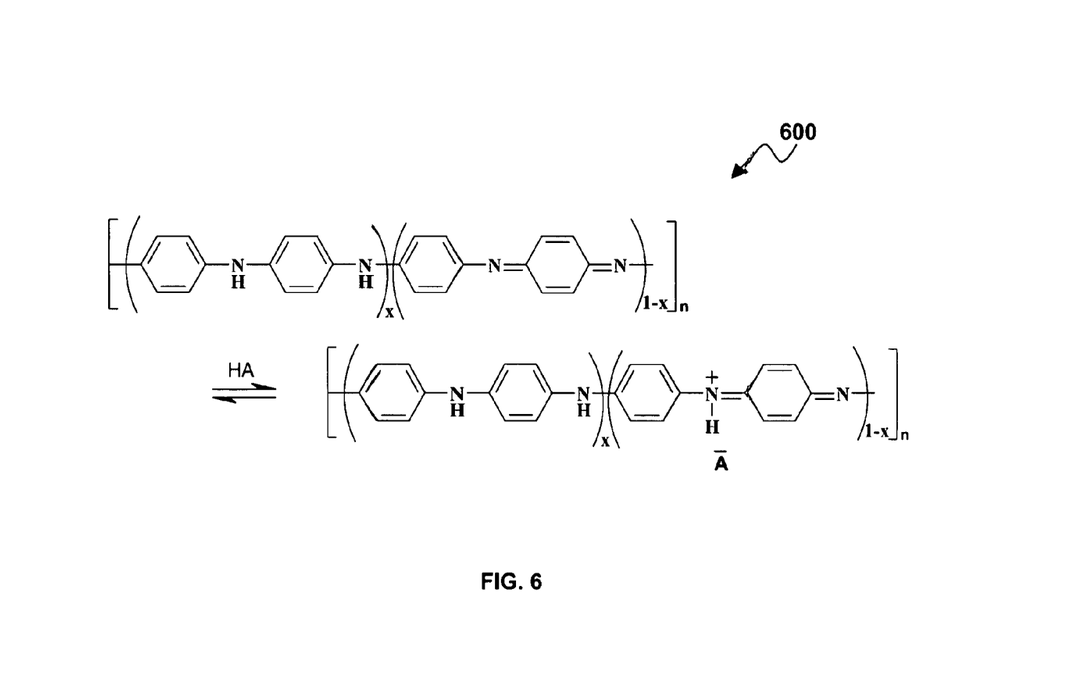
FIG. 6 illustrates a scheme for the doping of emeraldine, which can be implemented in accordance with a preferred embodiment.

Referring to FIG. 6, illustrated is a scheme for the doping of emeraldine, which can be implemented in accordance with a preferred embodiment. In order to dope emeraldine, the selected dopant was amino sulfonato carbon nanotubes, Polyaniline (0.5 g) as a free base was synthesized and placed in 40 ml dimethylformamide which contains 0.2 g of amino sulfonic group. Thereafter, the doped polyaniline was filtered and rinsed with water, in order to remove the unreacted dopant.

In order to construct the nanocomposite, a solution of amino CNTs was dispersed and sonicated in an appropriate solvent and mixed after that with a solution of doped polyaniline. Amino carbon nanotube was present in a composite in 5-15% (w/w). The matrix composite was deposited on the surface of transducer through traditional methods like spin coating, deep coating, spray coating, drop casting, or by a preferred way of direct printing.

The matrix nanocomposite based on amino derivatives and amino CNTs with electric interaction between the two components have advantages in comparison with the usual solution (polyaniline). Carbon nanotubes has amino groups, and thus can help to sensing. Due to the size of nanometer many amino groups are present at the surface of layer. Carbon nanotubes improve mechanical properties and can increase the life time of polymer due to the antioxidant character. Due to the strong electronic interaction between aromatic rings of polyanilines and aromatic rings of amino carbon nanotubes ($\pi$-$\pi$ stacking interactions) it can be expected to have a synergistic effect in detection of carbon dioxide molecules in SAW/BAW sensors.

Figure 7:
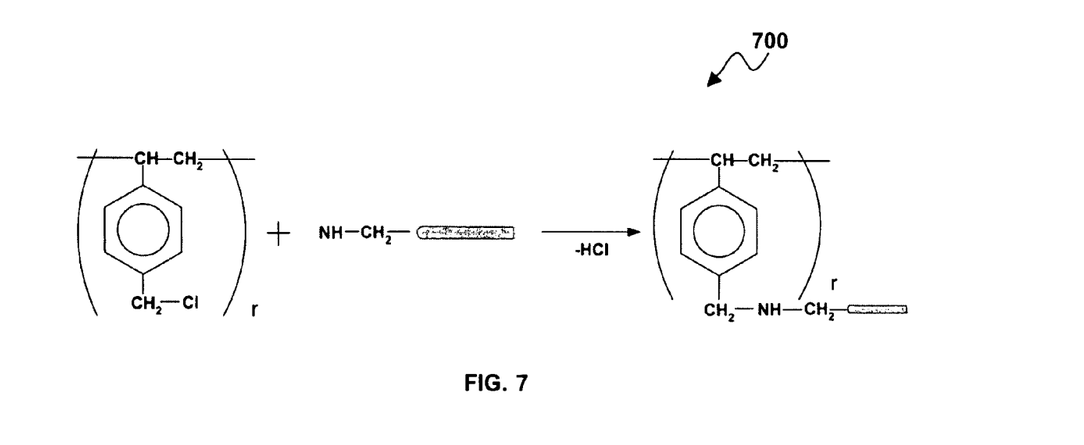
FIG. 7 illustrates a scheme for the synthesis of amino nanotubes based polymer from chloromethylated polystyrene and aminomethylcarbon nanotubes, which can be implemented in accordance with a preferred embodiment.

In the design of matrix nanocomposite with incorporation of amino carbon nanotubes in polymer uses chloromethylated polystyrene, chloromethylated polysulfone, brominated PPO as polymers which are functionalized with amino carbon nanotubes. Referring to FIG. 7, SCHEME. 3, 700, illustrates synthesis of amino nanotubes based polymer from chloromethylated polystyrene and aminomethylcarbon nanotubes, which can be implemented in accordance with a preferred embodiment. Chloromethylated polystyrene reacts in a nucleophylic displacement with aminomethyl carbon nanotubes and yields amino carbon nanotubes in polymer.

Figure 8:
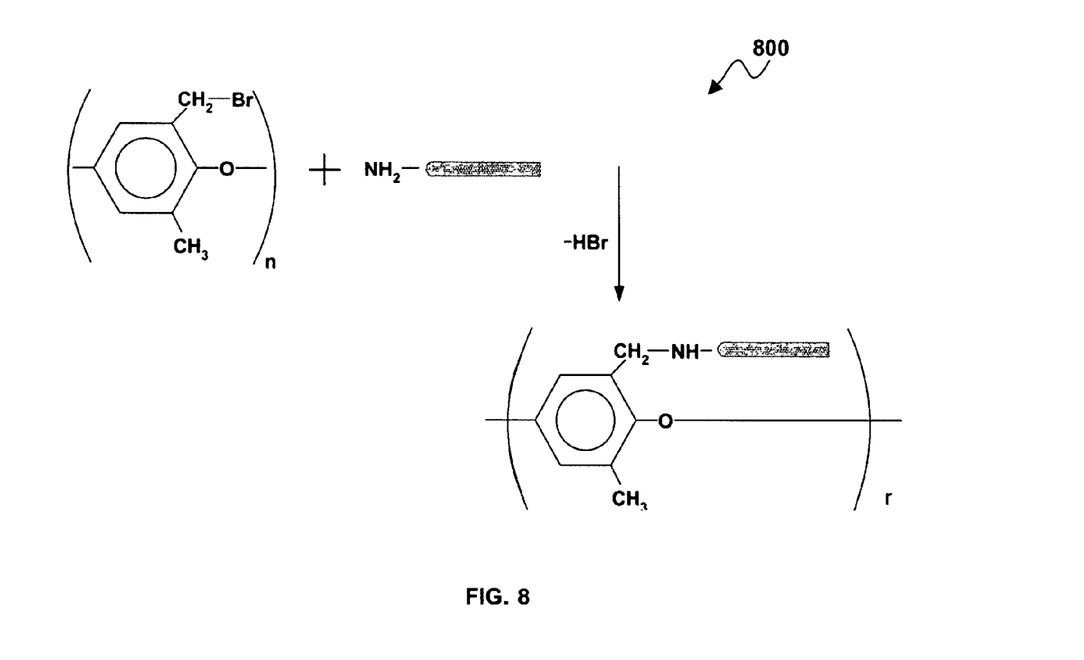
FIG. 8 illustrates a scheme for the synthesis of amino nanotubes based polymer from bromurated PPO (Poly Phenylene Oxide) aminomethylcarbon, which can be implemented in accordance with a preferred embodiment.

Referring to FIG. 8, illustrated is a scheme for the synthesis of amino nanotubes based polymer from brominated poly (2-,4-dimethyl-l, 6-phenylene oxide) aminomethylcarbon, which can be implemented in accordance with a preferred embodiment. Brominated 2, 6 dimethyl 1,4 phenylene oxide (PPO) reacts in a nucleophylic displacement with aminomethyl carbon nanotubes and yield amino carbon nanotube-based polymer. In order to construct the nanocomposite, a solution of amino CNTs was dispersed and sonicated in an appropriate solvent and mixed after that with a solution of amino CNT-based polymer. Amino carbon nanotube was present in a composite in 5-15% (w/w).

Figure 9:
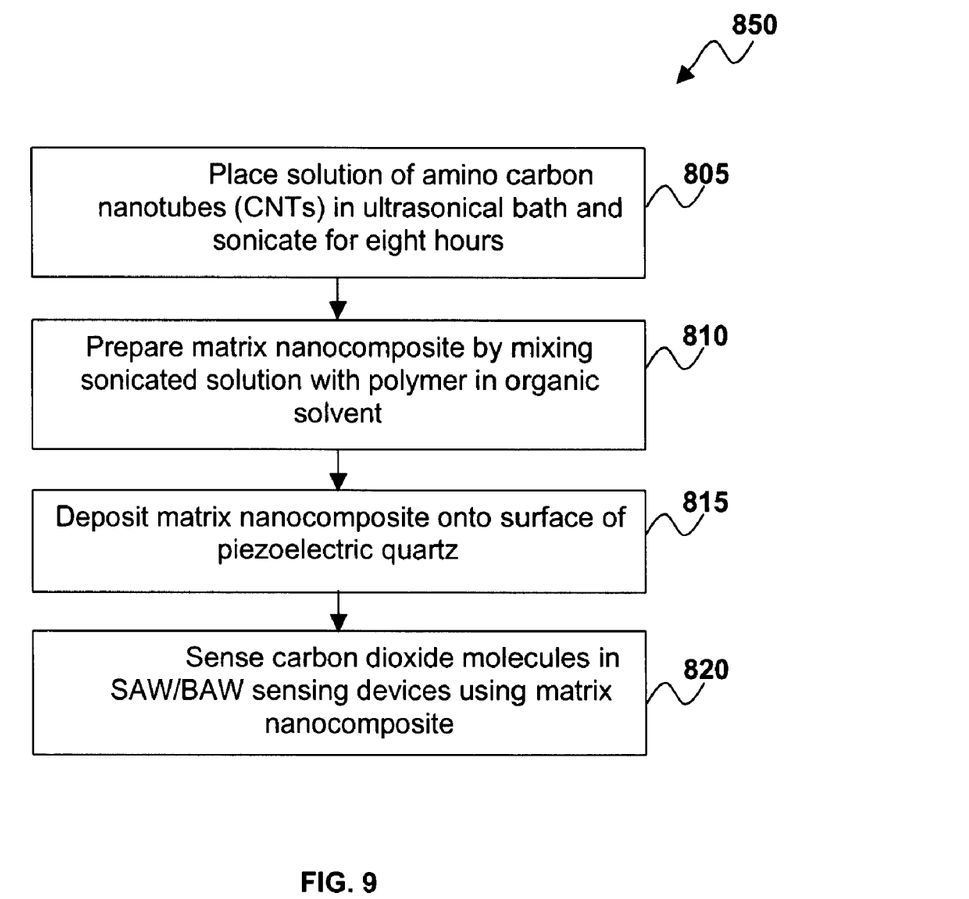
FIG. 9 illustrates a high level flow chart of operations depicting logical operational steps for designing and synthesis of matrix nanocomposite based on amino derivatives and amino carbon nanotubes without electric interaction between the two components.

FIG. 9 illustrates a high level flow chart 850 of operations depicting logical operational steps for designing and synthesis of matrix nanocomposite based on amino derivatives and amino carbon nanotubes without electric interaction between the two components. A solution of amino carbon nanotubes (CNTs) can be placed in an ultrasonical bath and sonicated for eight hours as said at block 805. As depicted at block 810, the matrix nanocomposite can be prepared by mixing sonicated solution with a polymer in an organic solvent. As indicated at block 815, the matrix nanocomposite can be deposited onto a surface of piezoelectric quartz. Finally, the carbon dioxide molecules in SAW/BAW sensing devices can be sensed using the matrix nanocomposite as said at block 820.

Figure 10:
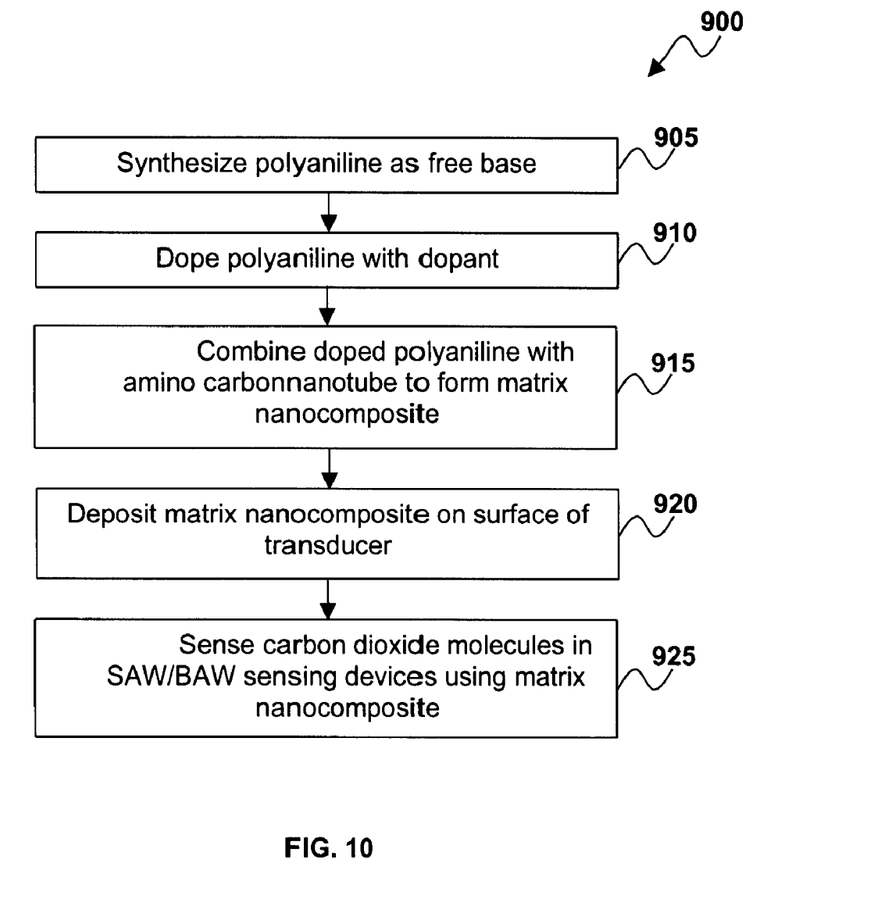
FIG. 10 illustrates a high level flow chart of operations depicting logical operational steps for designing and synthesis matrix nanocomposite based on amino derivatives and amino carbon nanotubes with electric interaction between the two components.

FIG. 10 illustrates a high level flow chart 900 of operations depicting logical operational steps for designing and synthesis matrix nanocomposite based on amino derivatives and amino carbon nanotubes with electric interaction between the two components. As said at block 905 polyaniline can be synthesized as a free base. As depicted at block 910 and 915, polyaniline can be doped with a dopant and the doped polyaniline can be combined with an amino carbonnanotube to form a matrix nanocomposite respectively. The matrix nanocomposite can be deposited onto a surface of a transducer as depicted at block 920. Finally, the carbon dioxide molecules in SAW/BAW sensing devices can be sensed using the matrix nanocomposite as indicated at block 925.

Figure 11:
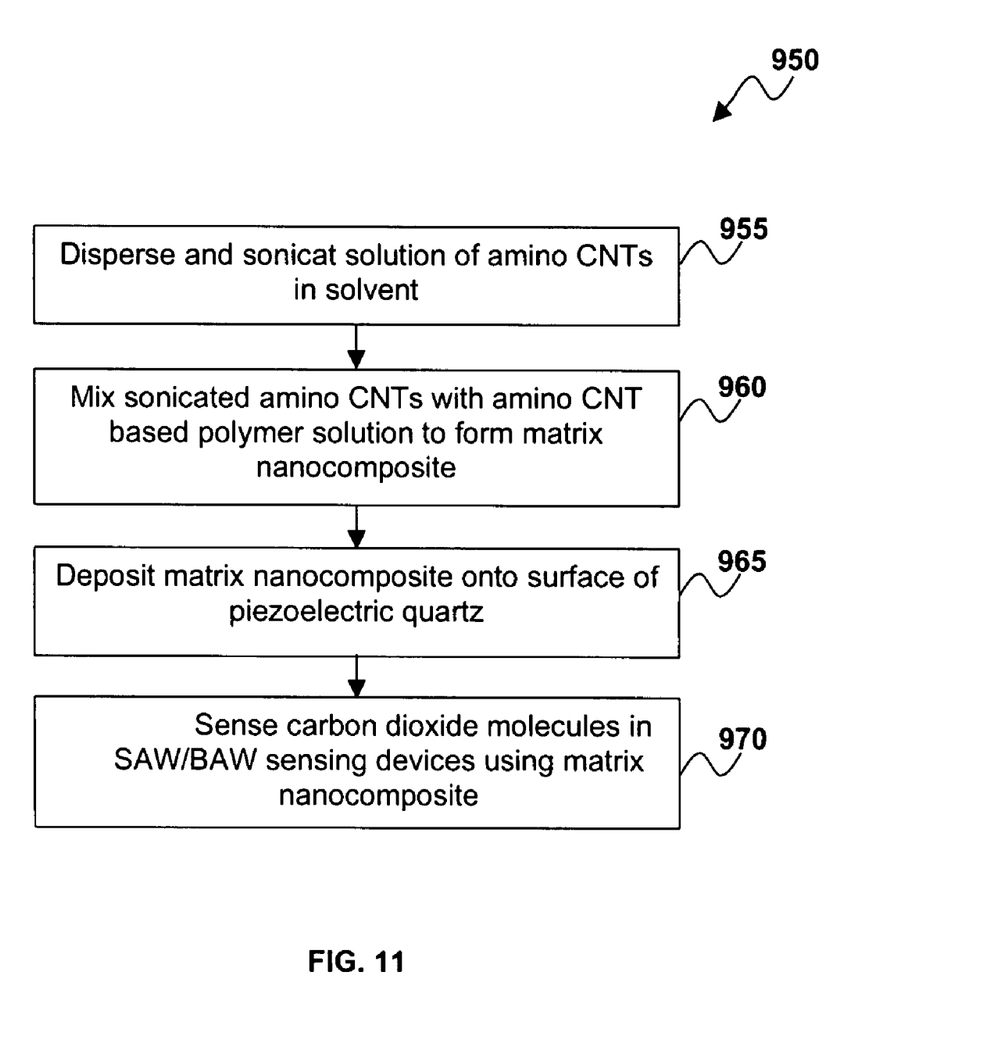
FIG. 11 illustrates a high level flow chart of operations depicting logical operational steps for designing and synthesis matrix nanocomposite with incorporation of amino nanotubes in polymer.

FIG. 11 illustrates a high level flow chart 950 of operations depicting logical operational steps for designing and synthesis matrix nanocomposite with incorporation of amino nanotubes in polymer. A solution of amino CNTs can be dispersed and sonicated in a solvent as indicated at block 955. As said at block 960, sonicated amino CNTs can be mixed with an amino CNT based polymer solution to form a matrix nanocomposite. The matrix nanocomposite can be deposited onto a surface of a transducer as depicted at block 965. Finally, the carbon dioxide molecules in SAW/BAW sensing devices can be sensed using the matrix nanocomposite as said at block 970.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A carbon dioxide sensor comprising;
    an acoustic wave device including a sensing layer deposited onto a surface of a piezoelectric quartz, said sensing layer comprised of a matrix nanocomposite containing aminocarbon nanotubes having amino groups that reversibly react with carbon dioxide to form carbamates, wherein said matrix nanocomposite comprises a polymer and at least one of single walled or multi-walled nanotubes present in said matrix nanocomposite between 5 and 15 percent.

2. The carbon dioxide sensor of claim 1, wherein said acoustic wave device is a surface acoustic wave (SAW) device.

3. The carbon dioxide sensor of claim 1, wherein said acoustic wave device is a bulk acoustic wave (BAW) device.

4. The carbon dioxide sensor of claim 1, said polymer comprises a conducting organic polymer which is sensitive to carbon dioxide.

5. The carbon dioxide sensor of claim 4, wherein said conducting organic polymer is selected from a group comprising: doped and undoped polyanilines (PANI).

6. The carbon dioxide molecule sensor of claim 1 wherein said matrix nanocomposite is deposited by direct printing.

7. A carbon dioxide molecule sensor comprising an acoustic wave device including a sensing medium adapted for use with an acoustic wave sensor, said carbon dioxide sensing medium further comprising a matrix nanocomposite of amino polymers combined with amino carbon nanotubes having amino groups that reversibly react with carbon dioxide to form carbamates, wherein said amino carbon nanotubes are present in said matrix nanocomposite between 5 and 15 percent.

8. The carbon dioxide molecule sensor of claim 7 wherein said polymer further comprises material from a group comprising:
    polyethyleneimine (PEI), Versamid 900, BMBT (N,N bis-(p-methoxybenzylidene)-α-α'-bi-p-toluidines), polyallylamines, polyvinylamines, diethanolamines, tryethanolamines and phthalocyanines (PC).

9. The carbon dioxide molecule sensor of claim 7 wherein said amino carbon nanotubes further comprise aminomethylcarbon nanotubes.

10. The carbon dioxide molecule sensor of claim 7 wherein said amino carbon nanotubes further comprise aminosulfonic carbon nanotubes.

* * * * *